United States Patent [19]

Al-Bayati

[11] Patent Number: 5,686,237
[45] Date of Patent: Nov. 11, 1997

[54] USE OF BIOMARKERS IN SALIVA TO EVALUATE THE TOXICITY OF AGENTS AND THE FUNCTION OF TISSUES IN BOTH BIOMEDICAL AND ENVIRONMENTAL APPLICATIONS

[76] Inventor: Mohammed A. S. Al-Bayati, 150 Bloom Dr., Dixon, Calif. 95620

[21] Appl. No.: 478,498

[22] Filed: Jun. 5, 1995

[51] Int. Cl.$^6$ .................. C12Q 1/00; G01N 33/544
[52] U.S. Cl. .................. 435/4; 435/6; 435/7.1; 435/7.9; 435/7.93; 435/7.94; 435/188; 436/528; 436/546; 436/144; 436/172; 436/810
[58] Field of Search .................. 435/4, 6, 7.1, 7.9, 435/7.93, 7.94, 188; 436/528, 546, 144, 172, 810

[56] References Cited

U.S. PATENT DOCUMENTS

| | | |
|---|---|---|
| 2,359,052 | 9/1944 | Scharer. |
| 3,153,616 | 10/1964 | Ito et al.. |
| 3,763,136 | 10/1973 | Huber et al.. |
| 4,053,363 | 10/1977 | Dorn. |
| 4,066,405 | 1/1978 | Henkin. |
| 4,385,125 | 5/1983 | Preti et al.. |
| 4,594,237 | 6/1986 | Ziegler. |
| 4,619,895 | 10/1986 | Cubicciotti. |
| 5,332,661 | 7/1994 | Adamczyk et al.. |

OTHER PUBLICATIONS

Alfonsky, D, 1961 *Saliva and Its Relation to Oral Health*. pp. 147–199. Paragon Press, Alabama.

Amdur, M. O. Doull, J., Klaassen, C.D., 1991. *Casarett and Doull's Toxicology. The basic science of Poisons*. Fourth Edition McGraw–Hill Inc.

Erdmann, E. 1980. Cardiac effects of vanadate. *Basics Res. Cardiol.* 75:411–412.

Friberg, L., Nordberg, G.F., and Vouk, V.B. 1986. *Handbook on the Toxicology of Metals*, vol. II, 2nd Edition, Elsevier.

Karlish, S.J.D. 1979. Vanadate inhibits (Na+ and K+) ATPase by blocking a conformational change of the unphosphorylated form. *Nature* 282:333–335.

Nechay, B.R. and Saunders, J.P. 1978. Inhibition by vanadium of sodium and postassium dependent adenosinetriphosphate derived from animal and human tissues. *J. Environ. Path. Tox.* 2:247–262.

Lopez, V., Stevens, T., and Lindquist, R.N. 1976. Vanadium ion inhibition of alkaline phosphatase–catalyzed phosphate ester hydrolysis. *Arch. of Biochem. and Biophys.* 175:31–38.

Phillips, T.D. 1982. Vanadium–induced inhibition of renal Na+, K+–ATPase in the chicken after chronic dietary exposure. *J. Tox. Env. Health* 9:651–661.

Tietz, N.W. 1986. Editor, *Textbook of Clinical Chemistry*. W.B. Sanders Company, Philadelphia.

Wang, T., Tsai, L., Solaro, R., Grassi de Gende, A., and Schwartz, A. 1979. Effects of Potassium on vanadate inhibition of sarcoplasmic reticulum Ca2+–ATPase from dog cardiac and rabbit skeletal muscle. *Biochem. Biophys. Res. Commun.* 91:356–361.

Borzelleca et al. *Journal Enviromental Sciences and Health*, "The Excretion of Pesticides in Saliva & its Value in Assessing Exposure," B 15(6), 843–866 (1980).

Nigg et al., *Chemosphere*, "Quantification of Human Exposure to Ethion using Saliva," vol. 26, No. 5, 897–906 (1993).

Eldefrawi et al., *Biomarkers of Human Exposure to Pesticides*, "Regulation of Muscarine Receptors as Biomarkers of Exposure to Insecticides," ACS 542, pp. 51–63, 1994.

Nauman et al., *Biomarkers of Human Exposure to Pesticides*, "Biomonitoring for Pesticide Exposure." ACS 542 (1994).

*Primary Examiner*—Paula K. Hutzell
*Assistant Examiner*—Khaled Masood
*Attorney, Agent, or Firm*—James M. Ritchey

[57] ABSTRACT

Sensitive methods using a variety of biomarkers in oral saliva of humans and animals to detect measure, and quantify the presence of infectious and non-infectious agents and the functional status of living tissues in both (1) biomedical and (2) environmental applications. With in vivo biomedical applications, saliva samples are taken from human and animals and biomarker, such as enzyme or antibody levels, are measured. The extent of exposure to an agents is measured by the presence of specific chemical or biological constituents, by the degree of enzymes inhibition, or by the changes in the amount of the biochemicals in saliva. With in vitro environmental applications, enzymes or other biochemicals from animal or human saliva can be used to monitor the presence of toxic or reactive agents in tissue samples, urine, feces, milk, air, water, soil, or plants. The amount of toxicant in samples is estimated from a standard curve for that agent.

5 Claims, 9 Drawing Sheets

5,686,237

USE OF BIOMARKERS IN SALIVA TO EVALUATE THE TOXICITY OF AGENTS AND THE FUNCTION OF TISSUES IN BOTH BIOMEDICAL AND ENVIRONMENTAL APPLICATIONS

BACKGROUND OF THE INVENTION

1. Field of the Invention

Generally, the present invention relates to the detection and measurement of biomaker in saliva. More particularly, the subject invention describes methods which employ saliva biomarker chemical species from human and animal subjects for detection, quantification, and evaluation of hazardous and toxic chemical or biological agents.

2. Description of the Related Art

The detection and quantification of potentially hazardous or toxic and potentially hazardous infectious biological agents are subjects of concern in biomedical and environmental fields as well as to the general public. Humans and animals are exposed to a wide variety of hazardous agents that may or may not be infectious endogenous xenobiotics. For example, on a world wide basis, pesticides have been estimated to cause as many as 500,000 illnesses annually, with as many as 20,000 deaths resulting from pesticide exposure. Information regarding the presence and quantity of hazardous agents within humans or animals, or in the environment where humans or animals may be exposed, is useful in prescribing medical treatments, avoiding further exposure, and assessing levels of environmental contamination.

Several fields of the biomedical sciences are concerned with the characterization and diagnosis of abnormal or pathologic conditions within the body of a human or animal. There are many types of neurological and systemic diseases leading to abnormal levels of specific biochemicals within the body. These biochemicals need to be detected and measured for the purpose of diagnosis. Currently, detection and measurement methods rely on tissue and blood samples which are used to monitor exposure to infectious agents or toxicants in human and animals or the presence of diseases and contaminating. The presently used techniques are generally limited to detecting tissue damage resulting from acute exposure to high levels of an agent, toxin, toxicant, and the like or tissue damage caused by advanced diseases or exposure to chemicals. The sensitivity of procedures utilizing blood or tissue samples is limited by many technical constraints which prevent detection at low levels of chemical agent or at early stages of diseases. For example, the chronic exposure to low levels of some organophosphate compounds and organic solvents can cause delayed neuropathy in human and animals, and the resulting changes in the nervous system cannot be monitored by currently used methods which characterize blood enzymes.

Acetylcholinesterase, carboxylase, and other enzymes present in blood and tissue have been used for many years as biomarkers to monitor the toxicity of both in vivo and in vitro. The presence of toxic or reactive agents in blood or tissue samples can often be detected by the degree of inhibition of one or more enzymes that are sensitive to binding and inhibition by those toxic or reactive agents.

The present invention introduces the use of human and animal saliva biomarkers for sensitive and non-invasive detection and quantification of chemical and biological agents, usually hazardous substances, including infectious and non-infectious agents. Several advantages are associated with the use of biomarker species that are enzymes from saliva as disclosed herein instead of from blood or tissue as previously carried out. For example, saliva biomarkers are exposed to toxic or reactive agents systemically through the blood and also locally by inhalation and/or ingestion through the mouth, while plasma and tissue enzymes are exposed only by blood uptake. This makes the intensity and the frequency of saliva exposure to toxicants greater than those in blood and tissues.

Another advantage is that saliva contains 0.2–0.5% protein, versus 7.2% in plasma, and the albumin content of saliva is 1% that of plasma. Chemicals or other hazardous agents may undergo nonspecific binding with various plasma proteins due to the high protein concentration, resulting in a reduction in enzyme sensitivity to the effects of the chemicals or other toxic agents. Still another advantage is the relatively small volume of saliva present in humans and animals, resulting in less dilution and higher concentrations of toxic. The volume of plasma (5 liters in adult human male) is much larger than the volume of saliva (0.8–1.0 liter produced per 24 hour), and the larger blood volume results in higher dilution of the toxic or reactive, making them more difficult to characterize.

Yet another advantage provided by oral saliva biomarkers is that the secretory cells of salivary glands are innervated by 5–10 parasympathetic neurons, and saliva probably contains true enzymes such as saliva cholinesterase which differs from the pseudo-cholinesterase present in plasma. Thus, the inhibition of true acetylcholinesterase from saliva is a better indicator for monitoring effects on the nervous system by a chemical agent than inhibition of the equivalent enzyme in plasma.

Additionally, collection of saliva does not require invasive procedures or special equipment as does the collection of tissues, blood, or plasma. The present invention only requires 1–2 mL of saliva for biomarker enzyme analysis.

Methods for protein fractionation and analysis of human saliva and the use of human saliva for detecting pregnancy are known. However, the presence of sensitive biomarkers species such as, but not limited to, acetylcholinestemse, carboxypeptidase, and carboxylase in saliva does not appear to have been reported, and the use of enzyme biomarkers from human and animal saliva for characterization of hazardous or toxic agents has not, it appears, heretofore been disclosed.

Accordingly, there is a need for a method of detecting, quantifying, and evaluating hazardous which provides for early detection, which can detect low levels of the, and which is not invasive and does not require blood or tissue samples from subjects. The present invention satisfies these needs, as well as others, and generally overcomes the deficiencies experienced in the background art.

SUMMARY OF THE INVENTION

The present invention pertains to new and sensitive methods which use saliva biomarker species from humans and animals to detect, measure, and quantify the presence of infectious and non-infectious hazardous and to evaluate the functional status of living tissues. Biomarker species contained in saliva are used in the subject invention to evaluate the toxicity of hazardous agents in two broad applications: (1) in vivo biomedical studies for internal bodily exposure of people or animals to the of interest, and (2) in vitro environmental measurements of the presence and/or concentration of the various or interest in environmental samples such as water, food, and the like. The presence of toxic or reactive in samples can be detected, for example, by the degree of inhibition of one or more biomarker enzymes present in saliva. The saliva provides a source of the enzymes that are inhibited by the agents of interest. For the subject invention, the inhibition of biomarker enzymes present in saliva provides a method for evaluating hazardous which appears to be more sensitive than currently available assay methods.

Generally, the invention method comprises the steps of acquiring or otherwise providing a saliva sample, analyzing or measuring the levels or concentrations of one or more biochemical constituents present in the saliva sample, and comparing the levels of the biochemical constituents in the sample with baseline levels or concentrations obtained or determined from control samples, standards, theoretical quantities, or specimens. Biomarker species present in the saliva sample, such as enzymes, antibodies, and other proteins, are responsive to various toxic or hazardous infectious and noninfectious agent, and the measured levels of biochemical constituents indicate the level of response of the biomarkers to the hazardous agents and thus the quantity of hazardous agent present.

In a first or in vivo embodiment of the invention, saliva samples are taken from human and/or animal subjects and biomarkers such as enzymes or antibodies in the saliva are monitored via inhibition or binding. Specifically, the presence of and extent of exposure to hazardous agents is measured by the presence and amount or level of specific chemical or biological constituents, by the degree of enzymes inhibition, by the amount of specific binding, or by the changes in the amount of the biochemical constituents in saliva. Using this embodiment, hazardous agents that inhibit carboxylase, acetylcholinesterase, alkaline phosphatase, acid phosphatase, amylase and other biomarker enzymes present in oral saliva are detected and quantified. Hazardous agents which inhibit these enzymes include, among others, organophosphate and carbamate pesticides and fluorophosphate nerve agents. The amount of hazardous agent present in the saliva is determined by comparison to a standard curve for the hazardous agent which is determined from control samples or theoretical predictions.

In a second or in vitro embodiment, enzymes or other biomarkers from animal or human saliva are used as a ready source for the biomarkers to monitor the presence of toxic or reactive agent in external or environmental samples from tissue, urine, feces, milk, air, water, soil, plants, or other sources. The amount of hazardous agent present in samples is determined from a standard or theoretical inhibition or binding curve for that agent. In one application of this embodiment, acetylcholinesterase and carboxylase (generally defined as enzymes having esterase-like activity) enzymes in human saliva are used to detect the presence of organophosphates such as pesticides in water samples with exceptional sensitivity.

By way of example and not of limitation, the analyzing step preferably is carried out by detecting and monitoring the level or concentration of one or more biochemical constituents in a saliva sample by spectrophotometric or chemical means. The biochemical constituents analyzed are indicative of the response of biomarker enzymes to various hazardous agents. The biochemical constituents may be reactive substrates which are specific for the biomarker enzymes, the reaction products of the biomarker enzymes and their specific substrates, the biomarker enzymes themselves, or other chemical or biological constituents present in a saliva sample which indicate the presence and quantity of a hazardous chemical agent. In the presently preferred embodiments, the analyzing step generally involves detecting inhibition of specific biomarker enzymes by spectrophotometrically monitoring (or monitoring by an equivalent method) reaction product formation and/or depletion of reactive substrates within the samples. The analyzing step also preferably includes measuring the overall amount of protein (this overall amount includes both enzymes and non-enzyme protein components) present in the saliva sample.

The invention may also include the step of determining baseline levels of biochemical constituents from standard or control saliva samples. Generally, standard curves for biochemical constituents which reflect biomarker enzyme activity are prepared from control samples. The determining step also preferably includes determining baseline levels for the overall protein content of saliva samples.

The in vitro embodiment of the invention preferably also includes the steps of obtaining or extracting and concentrating hazardous from environmental, tissue, or other samples. Purification and concentration of the saliva sample may also be carried out in this embodiment. Evaluation of the toxicity of new or unknown infectious or non-infectious hazardous agents may be carried out using the in vitro embodiment.

The present invention has scientific value and has several applications with significant commercial potential. The scientific value is exemplified by the discovery of the presence of biomarkers such as acetylcholinesterase and carboxylase enzymes in human saliva and the use of such saliva enzymes to evaluate exposure of human and animals to hazardous agents in both in vivo and in vitro settings. These biomarkers can also be used to monitor changes in human and animal health that result from exposure to endogenous compounds. Purified human and animal saliva enzymes to be used in clinical, research, industrial, and military applications, as well as by the general public to evaluate the, presence, quantity, and toxicity of agents may be provided.

Test kits can be fabricated that utilize the subject methods with related equipment for biomarker enzyme assays. The kits can also be used to detect residue of chemical and biological toxicants in milk and other biological fluids, animal and plant tissues, water, air, and soil samples. Test kits and equipment may be used by agriculture workers, industrial hygienists, military personnel, researchers, and members of the general public.

An object of the invention is to provide a method for detection, quantification, and evaluation of hazardous agents which utilizes biomarkers present in oral saliva of humans and animals.

Another object of the invention is to provide a method for detection, quantification, and evaluation of hazardous agents which is quick and facile to use and which does not require expensive equipment or extensive training.

Another object of the invention is to provide a method for detection, quantification, and evaluation of hazardous agents which allows sensitive and accurate characterization of agents present in low levels.

Another object of the invention is to provide a method for detection, quantification, and evaluation of hazardous agents which allows both in vivo and in vitro characterization of agents.

Another object of the invention is to provide a method for detection, quantification, and evaluation of hazardous agents which is non-invasive and does not require blood or tissue samples.

Another object of the invention is to provide a method for detection, quantification, and evaluation of hazardous agents which may be used in kit forms.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DETAILED DESCRIPTION OF THE PREFERRED EMBODIMENT

Referring to FIGS. 1-15, as well as the following detailed description, the present invention is embodied in the process generally described herein. It will be appreciated that the invention may vary as to details and as to sequence in the steps of the process without departing from the basic concepts as disclosed herein.

In using the method comprising the present invention, the presence in human or animal subjects of and extent of exposure to hazardous agents is evaluated by analyzing the presence and amount, level, or concentration of specific chemical or biological constituents (hereinafter collectively referred to as biochemical constituents), by the degree of inhibition of one or more enzymes, or by the changes in the amount of the biochemical constituents in saliva. In the presently preferred embodiments, the degree of biomarker enzyme inhibition is generally followed by detecting and monitoring levels or concentrations of reaction direct or indirect (or linked) products from particular biomarker enzymes and their specific substrates. It is noted that substrate usage is acceptable for following the inhibition kinetics of the appropriate reaction. The detected levels or concentrations of reaction products are then compared with baseline levels or concentrations of the same reaction products in the form of a standard curve obtained from control or standard samples or specimens. Differences between the monitored and baseline levels of the reaction products reflect the degree of inhibition of the biomarker enzymes and thus the presence and amount of the inhibiting hazardous agent.

Figure 1:
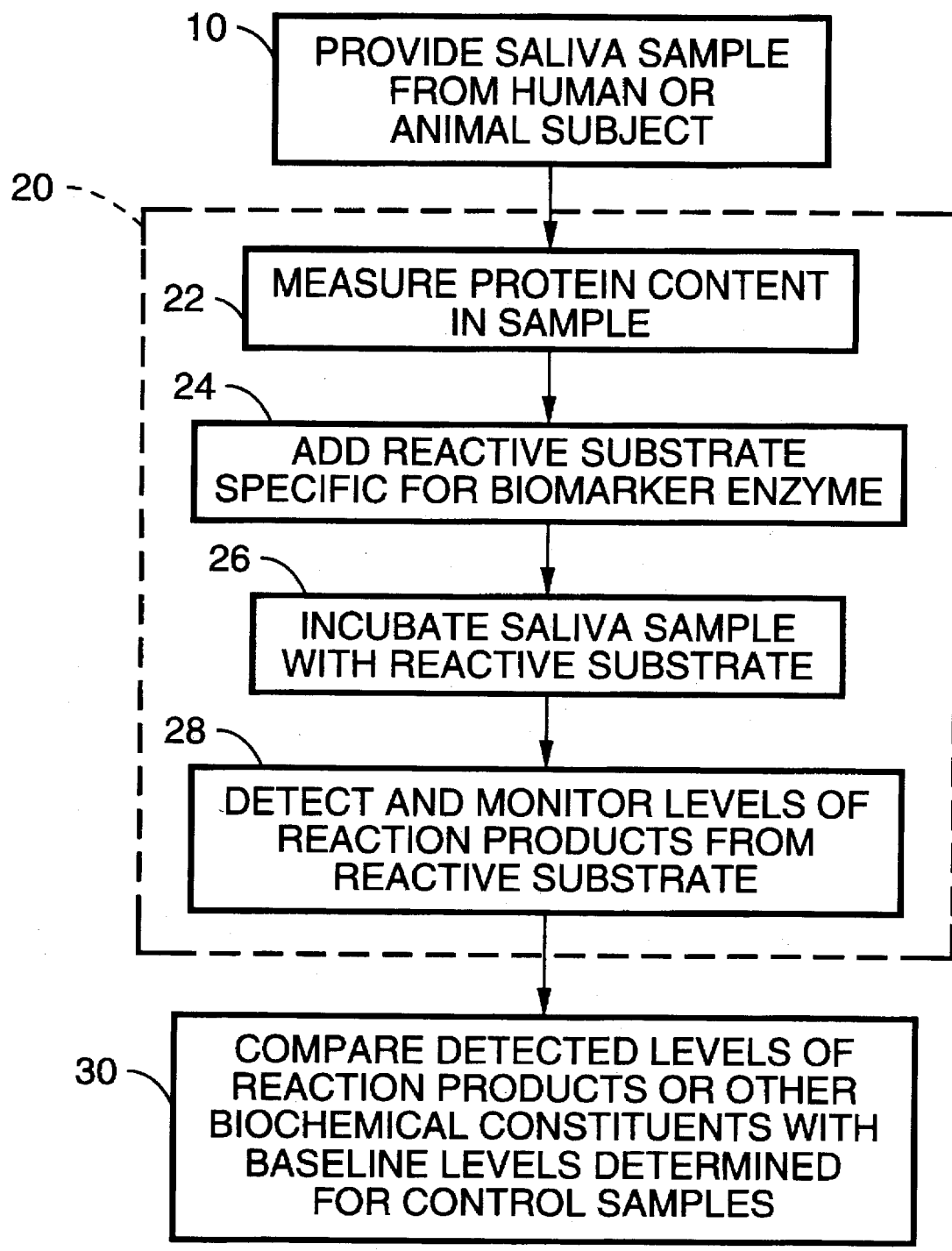
FIG. 1 is a flow diagram showing or in ally the method steps in a first or in vivo embodiment of a method for using saliva biomarkers to monitor and evaluate toxic agents.

Referring first to FIG. 1, there is shown a flow chart which generally outlines the steps of a first or in vivo embodiment of a method for evaluating, monitoring, and quantifying hazardous agents which may be present in a human or animal subject. At step 10, an oral saliva test sample is acquired, provided, or otherwise obtained from a human or animal subject. The method of obtaining the sample can be varied. Only about one to two milliliters of saliva per test sample are required for use with the present invention, making this method particularly easy and non-invasive to carry out. The saliva sample contains numerous naturally present biomarkers, in particular for the subject invention, enzymes, antibodies, and other biochemical constituents. The presently preferred biomarkers employed in the invention include carboxylase, acetylcholinesterase, carboxypeptidase, alkaline phosphatase, acid phosphatase, amylase, and other esterases naturally present in human and animal saliva.

At step 20, biochemical constituents in the saliva sample are analyzed. Generally, the analyzing step comprises the detection and monitoring of levels or concentrations of one or more biochemical constituents. The biochemical constituents analyzed in this step may include reactive substrates specific for biomarker enzymes, the biomarker enzymes themselves, reaction products of the substrates and biomarker enzymes, or any proteins or biomolecules present in the saliva sample. The biochemical constituents analyzed may be naturally present in the saliva sample or added thereto during the analyzing step, as in the case of certain easily detectable substrates and substrate reaction products. Preferably, the biochemical constituents analyzed in this step are ones which may be detected and monitored by spectrophotometric or colorimetric means or other easily applicable techniques that are readily usable in laboratory and non-laboratory or field conditions where sophisticated instruments are limited. Standard or later developed chemical detection and monitoring means may also be employed. The detection is preferably by visible spectrophotometry, allowing monitoring of sample optical density or transmission at wavelengths for specific chemical or biochemical constituents.

As related above, the presently preferred in vivo embodiment involves monitoring the inhibition of biomarker enzymes by hazardous agents by detection and monitoring reaction products of the biomarker enzymes with specific substrates. For reasons of clarity, the analyzing step is shown as sub-steps 22, 24, and 26 are shown in the analyzing step 20 to more clearly show the presently preferred in vivo embodiment. As used in this disclosure, the term in vivo implies the monitoring of inhibition of salival biomarker enzymes by hazardous agents that are directly present in the sample saliva or elsewhere in the body as opposed to in vitro cases where the utilized saliva has the hazardous agent or agents introduced after acquisition for measurement purposes.

At sub-step 22, the overall protein content of the saliva sample is analyzed and measured. The protein content measurement is generally carried out on an aliquot of the saliva sample by standard visible spectrophotometric means as related by Lowry et al. in "Protein Measurement with the Folin Phenol Reagent", *J. Biol. Chem. Vol.* 193, pp. 265–275 (1951), which is herein incorporated by reference. It is noted that other equivalent protein determination methods are acceptable. Generally, bovine serum albumin or gamma-globulin are used as reference standards, with the protein concentration values determined by comparison with a standard curve. Human saliva generally contains about 0.2–0.5% protein by weight. This protein measurement is necessary for calculating the specific activity of the biomarker enzymes monitored in analyzing step 20. The specific activity of the biomarker enzymes is a relative measurement based on the total protein concentration and not necessarily the concentration of any one specific enzyme of enzymes.

At sub-step 24, one or more reactive substrates specific for one or more biomarker enzymes are added to the saliva sample, to serve as biochemical constituents to be analyzed directly or via linked assay procedures common in the art. Preferably, the added reaction substrate measure directly and is therefore one which forms easily detectable reaction products upon reaction with its specific biomarker enzyme. For a linked assay, additional chemicals or indicators may be added in this step to form biochemical constituents which are easily detected. In one application of the in vivo embodiment, as related in the experimental section below, the substrate p-nitrophenylvalerate, which is specific for the biomarker enzyme carboxylase, is added to the saliva sample and forms the hydrolysis product p-nitrophenol which can be detected and monitored spectrophotometrically at 400 nm. In another application of this embodiment, the substrate acetylthiocholine iodide is added to the saliva sample, and is hydrolyzed by acetylcholinesterase to yield, after the addition of 5,5-dithiobis-2-nitrobenzene, a colored species which can be detected spectrophotometrically at 405 nm. It is also contemplated that substrates and their reaction products which are naturally present in saliva could be detected and monitored.

The analyzing step 20 generally includes an incubation sub-step 26, wherein the saliva sample and the added reaction substrates or other added biochemical constituents are allowed to react prior to detection and monitoring of reaction products. Preferably, though not critically, samples are incubated at about 37° C. in a suitable temperature controlled bath. The incubation period and temperature may vary depending upon the reactive substrate and biomarker enzymes being analyzed. Ambient temperature incubation or no incubation at all may suffice, again depending upon the nature of the biochemical constituents to be analyzed.

At sub-step 28, the reaction products from the specific substrate and biomarker enzyme are detected and monitored, usually by spectrophotometric means, preferably by visible spectrophotometric means as related above. The detection and monitoring indicates the level or concentration of the reaction products or other biochemical constituents present in the saliva sample (or in the case of reaction substrate evaluations the level or concentration of the substrate). The activity of the biomarker enzyme in the saliva sample can be calculated from the level or concentration of reaction product (or substrate) obtained in this sub-step.

At step 30, the levels or concentrations of the biochemical constituents are compared to standard or baseline levels for the biochemical constituents which are obtained from control or standard samples or specimens. The standard or base line level is preferably in the form of a standard curve showing the level, concentration, or other characteristic of the biochemical constituents analyzed in the previous step 20. In the preferred embodiment, the standard curve is one for biomarker enzyme activity which is obtained by inhibition studies in a plurality of control saliva samples. Comparison of the biomarker enzyme activity from the test sample to the standard curves accurately indicates the presence and amount of particular hazardous agents.

The in vivo embodiment may also include the step of determining the base line levels of the biochemical constituents (not shown) to be used in the comparing step 30. This step is generally carried out by adding test compounds or hazardous agents to control samples and incubating, followed by analyzing biochemical constituents in the sample, preferably in the form of substrate reaction products as related above. A biomarker enzyme activity standard curve is prepared from data from the control samples, and used in the comparing step 30.

Using the in vivo embodiment of the invention above, sensitive biomarkers can be used to monitor the exposure of people and animals to enzyme inhibiting toxic or reactive agents at low levels and it can be used to quantify the extent of exposure at a stage when the process is hopefully readily reversible. In particular, human saliva contains measurable activity of acetylcholinesterase and carboxylase biomarker enzymes. The activities for carboxylase and acetylcholinesterase are about 47–79 and about 4 nmol min$^{-1}$ per mL of saliva, respectively, as related below in the experimental section. These two biomarker enzymes are inhibited by isofenphos (IFP), des N-Isofenphos-oxon (DNIO) and paraoxon organophosphates. The effective concentration for 50% inhibition $EC_{50}$ for both carboxylase and acetylcholinesterase by DNIO is 3 ng/mL. The detection limit of DNIO by gas chromatography is 10,000 ng/mL, in comparison. Detection of DNIO using saliva biomarker enzymes is thus 3500 time more sensitive than measuring DNIO by gas chromatography (GC). These data indicate that the enzymes in saliva of human and animals can be used with the present invention as very sensitive biomarkers to evaluate the degree of exposure to toxicants and to quantify the extent of exposure at a stage when the process is readily reversible.

There are numerous other hazardous agents which inhibit carboxylase and acetylcholinesterase and which may be detected, quantified, and evaluated in vivo using the present invention. For example, human or animal exposure to other organophosphate insecticides, carbamate insecticides, blue green algae-anatoxicant-A, solanum specious black nightshade (*S. nigrum*), potato (*S. tuberosum*), horse nettle (*S. tuberosum*), European bittersweet (*S. dulcamara*), Jerusalem cherry (*S. pseudocapsicum*), as well as other noninfectious and infectious hazardous agents.

While the preferred in vivo embodiment of the invention as related above is described generally as it is used to detect and quantify inhibition of carboxylase and acetylcholinesterase by organophosphates, it should be readily apparent to persons skilled in the art that the invention may be used in evaluating a variety of infectious and non-infectious hazardous agents. Examples of hazardous noninfectious agents contemplated for detection, quantification, or evaluation with the present invention include carbamates and other pesticides, nerve agents, mustard agents, biotoxicants, heavy metals, and endogenous compounds. Hazardous infectious agents considered for evaluation with the present invention include viruses, mycoplasmas, bacteria, parasites, yeast, and fungus. These hazardous agents have detectable effects on various biomarkers present in saliva, and may be evaluated using the in vivo embodiment.

Biomarkers other than enzymes may also be employed with the invention. For example, antibodies present in saliva may be analyzed for binding with antigens to evaluate the toxicity in humans and animals of infectious agents. The in vivo embodiment of the invention may also be used to evaluate toxicity in humans and animals from endogenous compounds resulting from organ malfunctions, such as acholinesterasemia in the liver. The presence of various biochemical constituents in saliva can be used to evaluate various tissue and organ malfunctions or potential malfunctions. The in vivo embodiment of the present invention thus provides a powerful medical diagnostic method which is easy to use and is non-invasive, requiring only small amounts of saliva samples from subjects.

Figure 2:
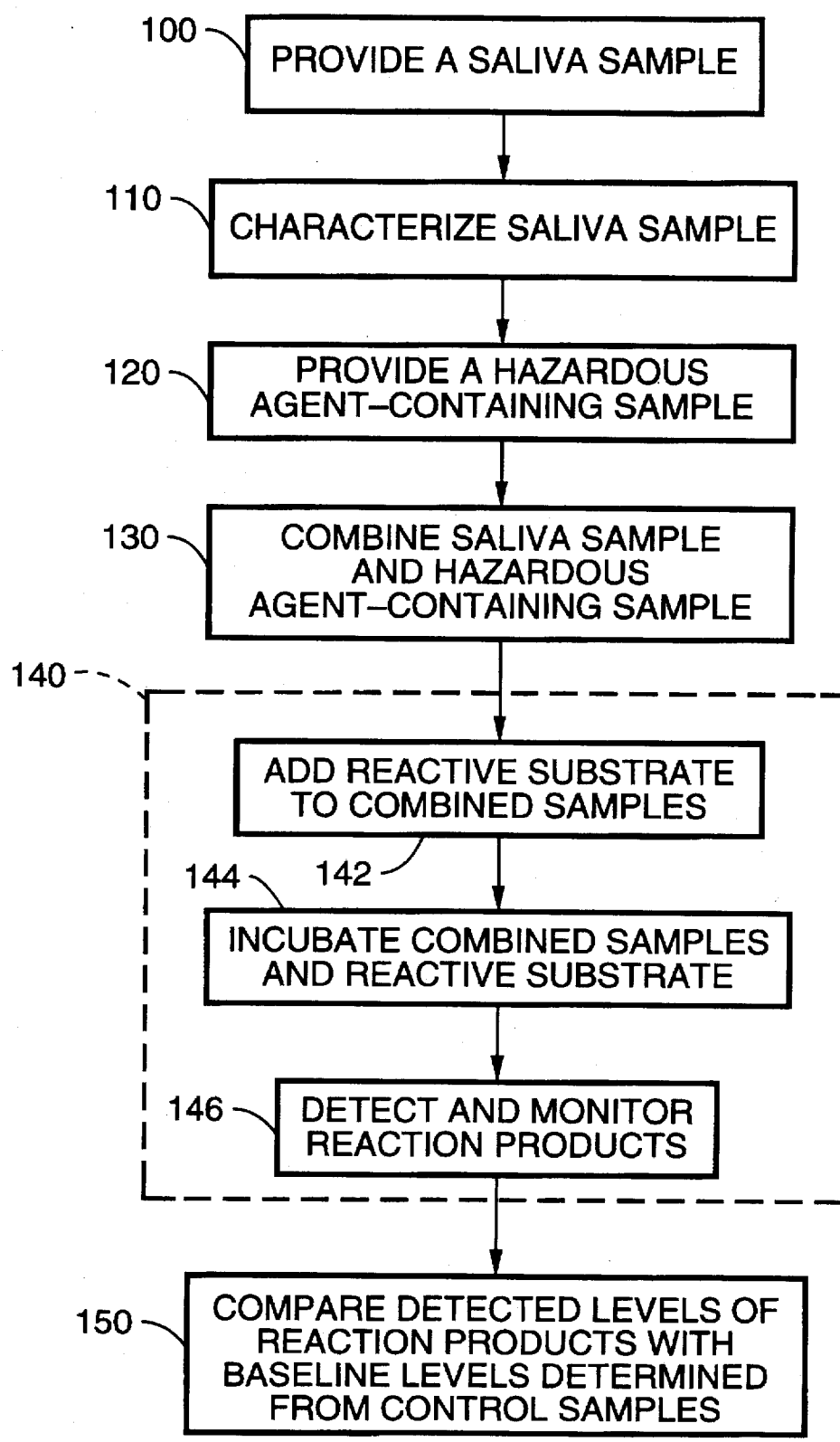
FIG. 2 is a flow diagram showing generally the method steps in a second or in vitro embodiment of a method for using saliva biomarkers to monitor and evaluate toxic agents.
Figure 3:
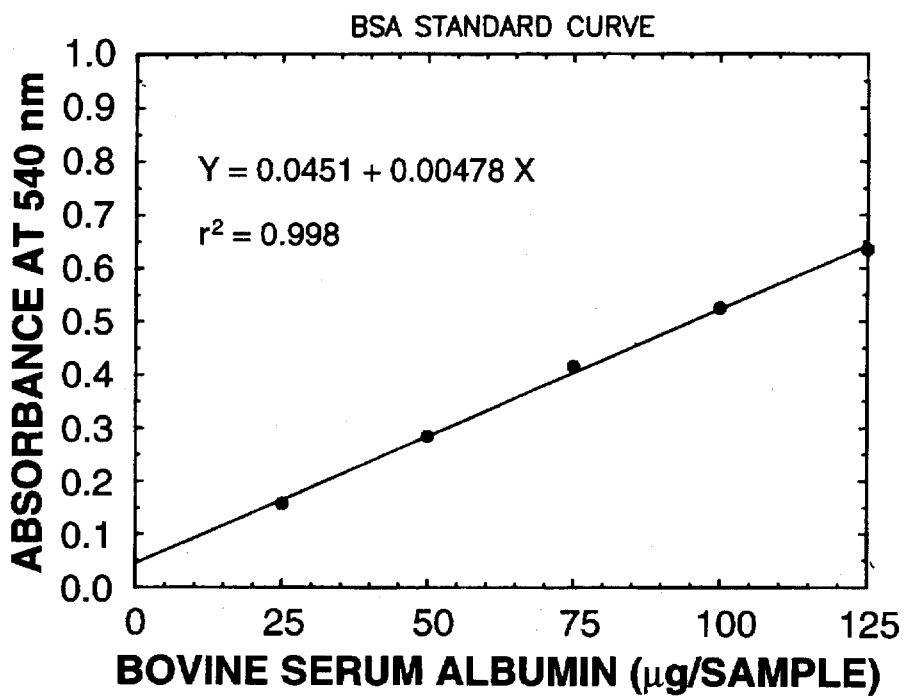
FIG. 3 is a graphic representation of a bovine serum albumin absorbance curve.
Figure 4:
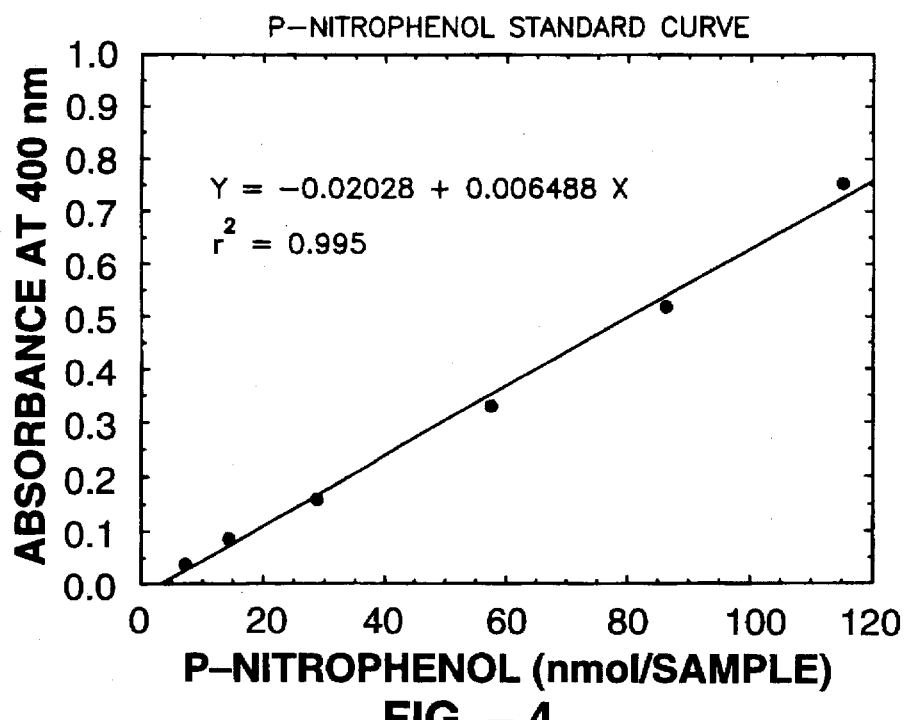
FIG. 4 is a graphic representation of a p-nitrophenol absorbance curve.
Figure 5:
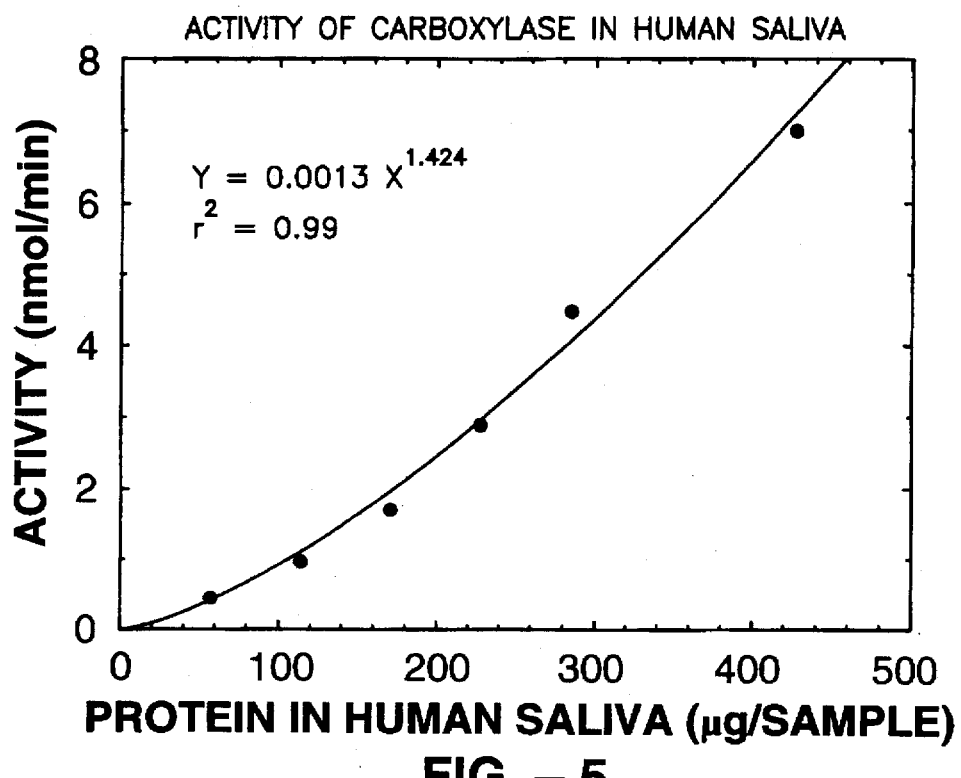
FIG. 5 is a graphic representation of the activity of carboxylase in human saliva versus protein in saliva (µg) in a 4 mL sample.
Figure 6:
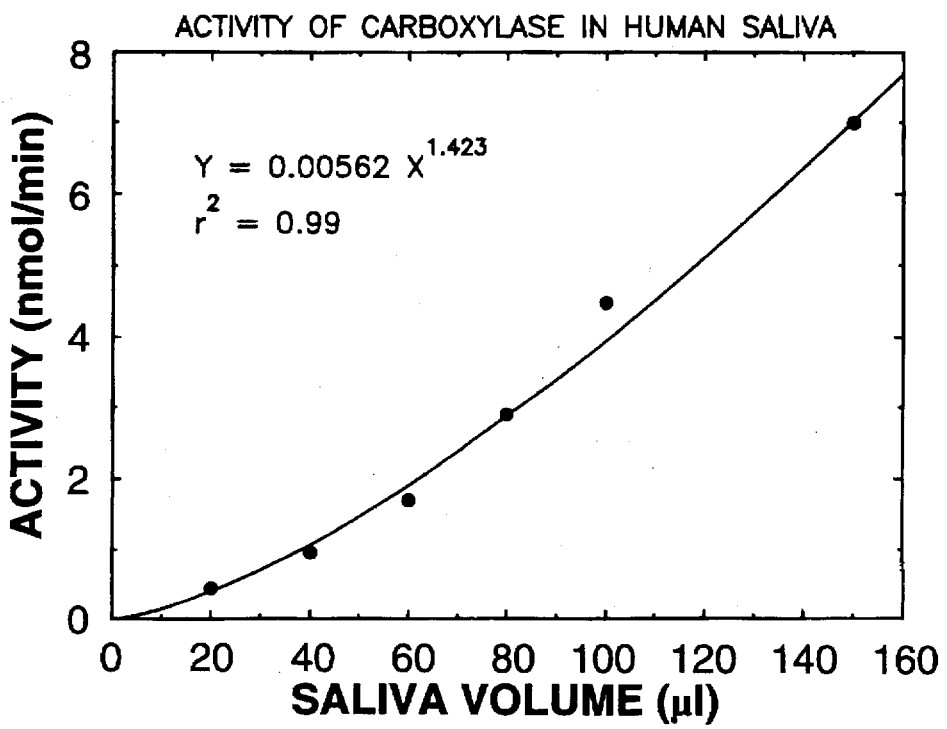
FIG. 6 is a graphic representation of the activity of carboxylase in human saliva versus saliva (µl) in a 4 mL sample.
Figure 7:
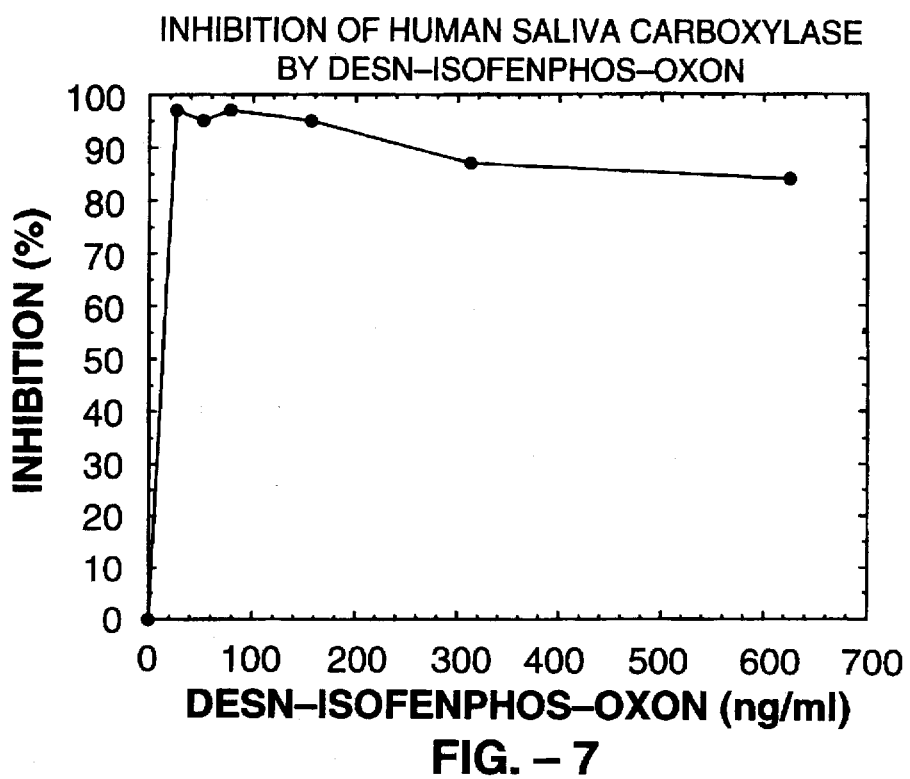
FIG. 7 is a graphic representation of the percent of carboxylase inhibition in human saliva by organophosphate pesticide in vitro.
Figure 8:
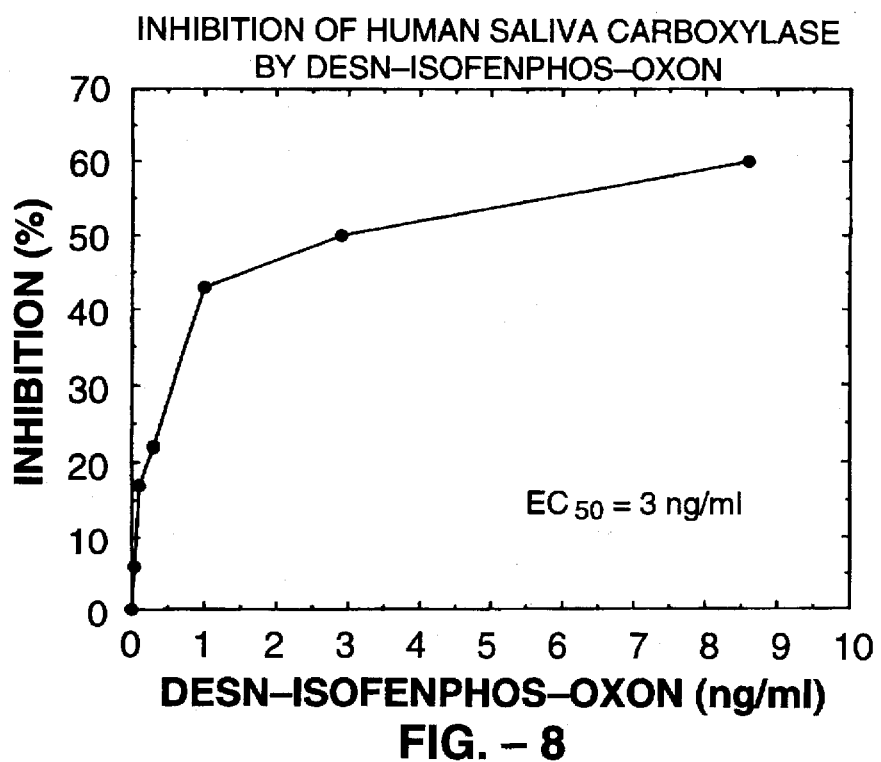
FIG. 8 is a graphic representation of the percent of carboxylase inhibition in human saliva by organophosphate pesticide.
Figure 9:
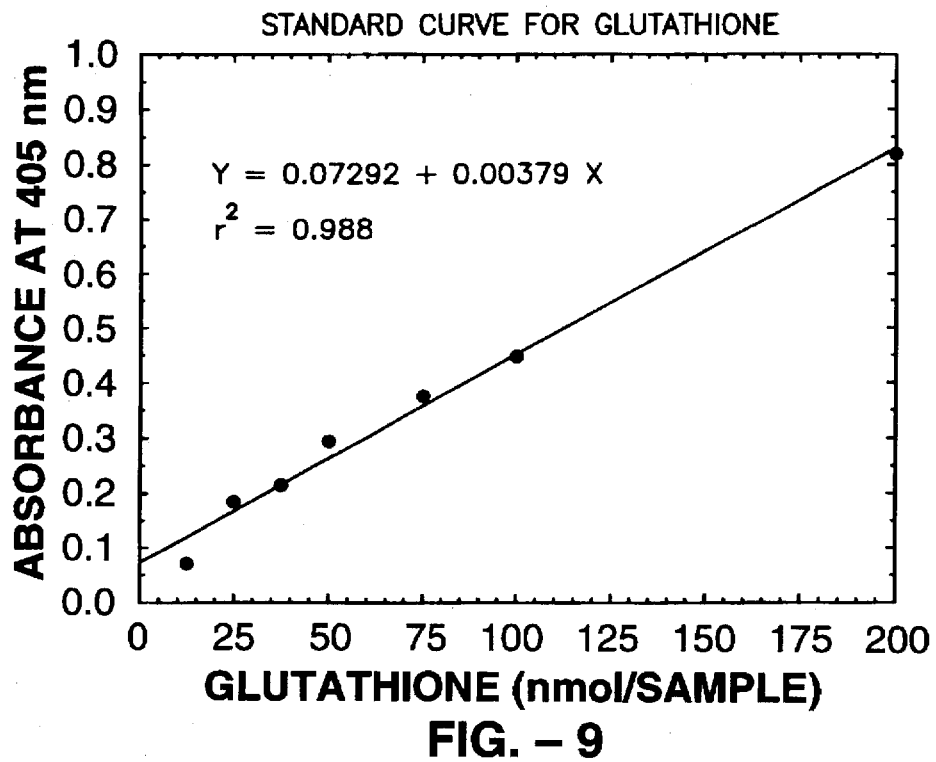
FIG. 9 is a graphic representation of a glutathione absorbance curve.
Figure 10:
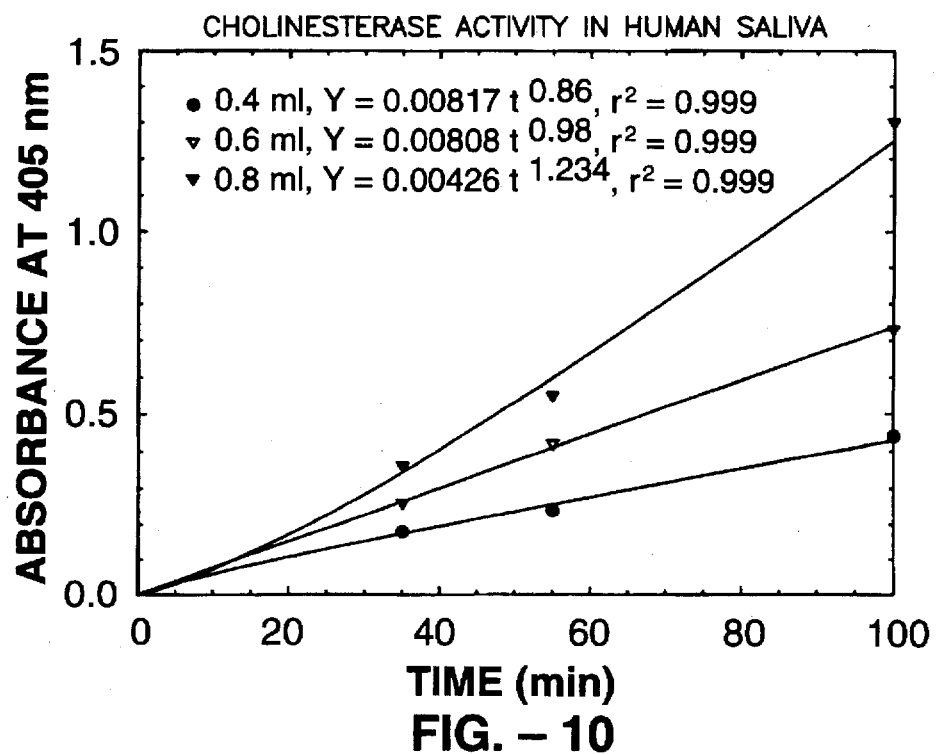
FIG. 10 is a graphic representation of the activity of acetylcholinesterase in human saliva versus incubation time minutes for three saliva concentrations.
Figure 11:
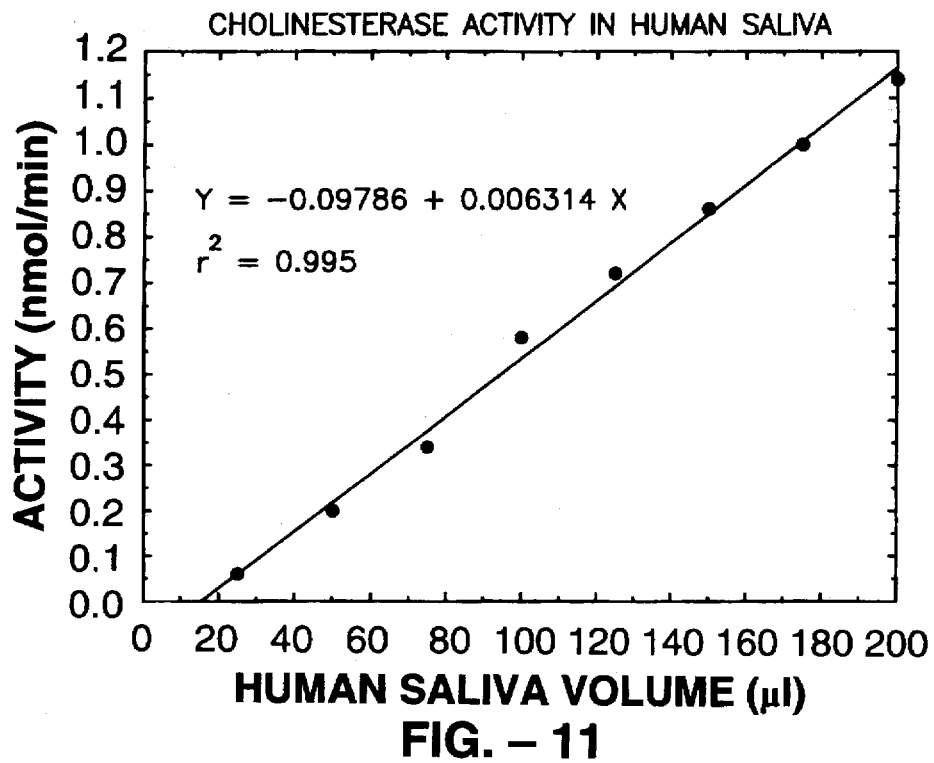
FIG. 11 is a graphic representation of the activity of acetylcholinesterese in human saliva versus saliva (µl) per 4 mL (incubation time =165 minutes).
Figure 12:
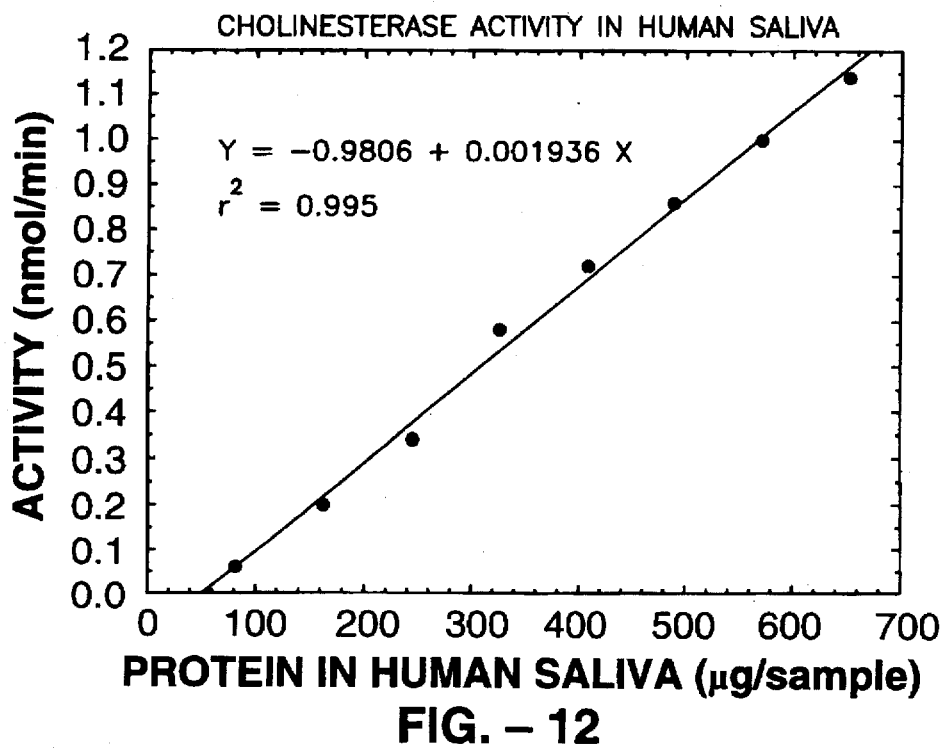
FIG. 12 is a graphic representation of the activity of acetylcholinesterase in human saliva versus protein content in saliva (µg) per 4 mL (incubation time =165 minutes).
Figure 13:
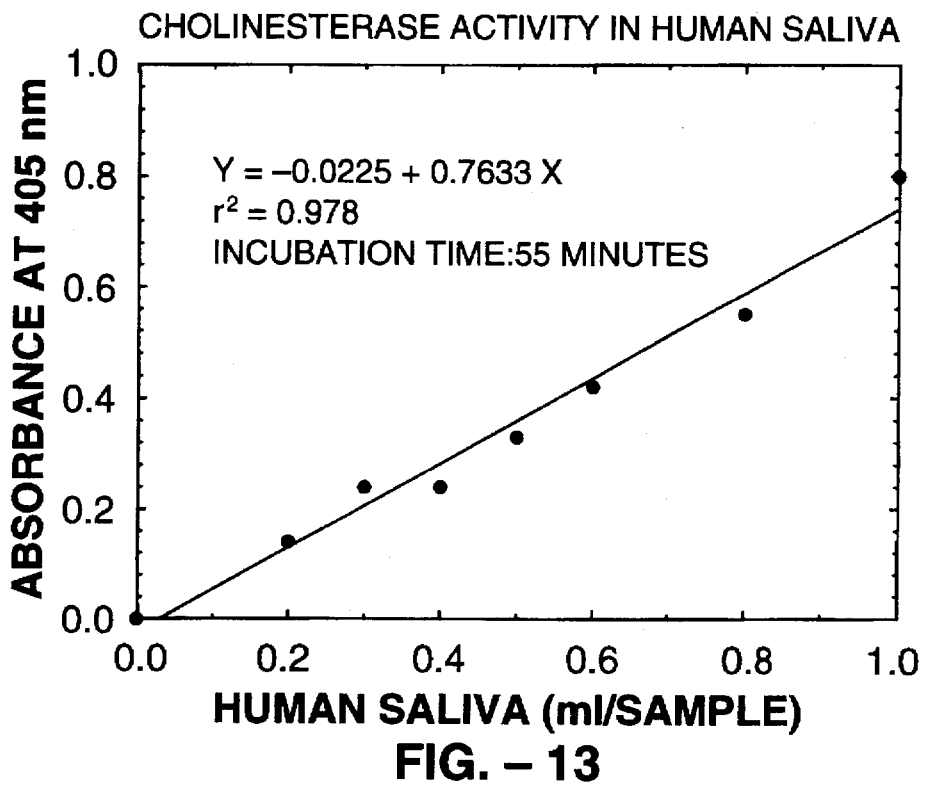
FIG. 13 is a graphic representation of the activity of acetylcholinesterase in human saliva versus volume saliva (mL)in 4 mL.
Figure 14:
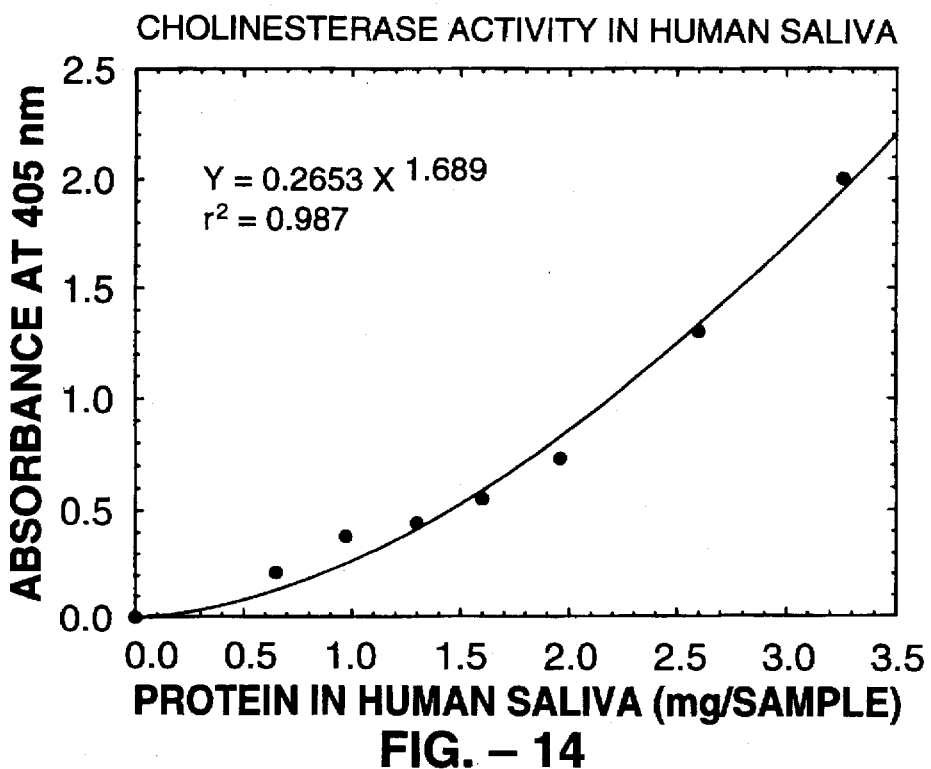
FIG. 14 is a graphic representation of the activity of acetylcholinesterase in human saliva versus protein content in saliva (mg) in 4 mL.
Figure 15:
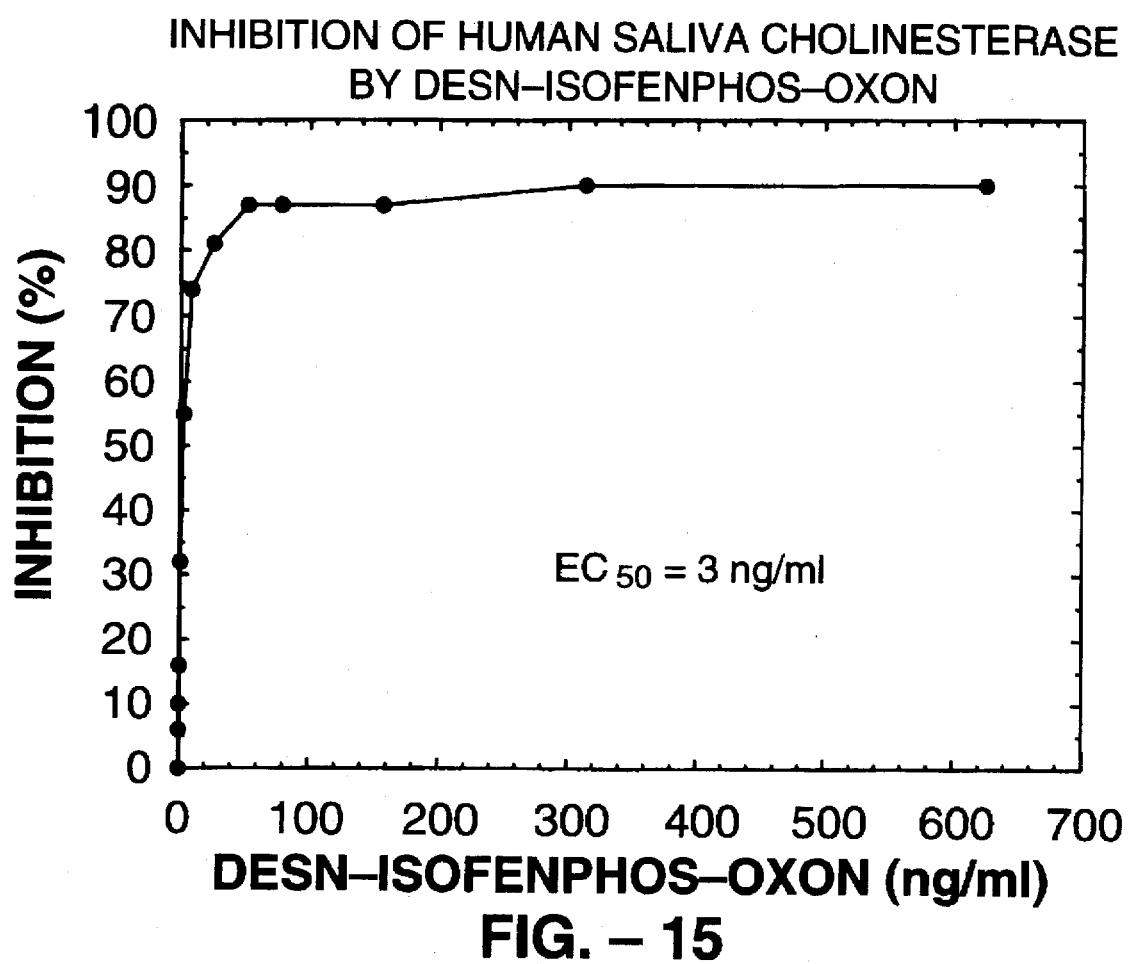
FIG. 15 is a graphic representation of the percent of acetylcholinesterase inhibition in human saliva by DNIO.

Referring next to FIG. 2, there is shown a flow diagram which generally outlines the steps of a second or in vitro embodiment of the present invention. In this embodiment, biomarkers in saliva samples are used to evaluate hazardous agents present in external or in vitro samples from sources other than the saliva containing the biomarker enzymes, rather than hazardous agents present in vivo in the saliva or in the body of human and animal subjects. As with the in vivo embodiment related above, the degree of biomarker enzyme inhibition is preferably monitored by detecting and monitoring levels or concentrations of reaction products (or substrate concentration) from particular biomarker enzymes and their specific substrates. The detected levels or concentrations of reaction products are then compared with baseline levels or concentrations of the same products in the form of a standard curve obtained from control or standard samples or specimens. Differences between the monitored and baseline levels of the reaction products reflect the degree of inhibition of the biomarker enzymes and thus the presence and amount of the inhibiting hazardous agent.

At step 100, a saliva sample is acquired, obtained, or otherwise provided by any suitable technique. As in the in vivo embodiment, only about one to two milliliters of saliva per test sample are usually required. The same naturally present biomarkers related above may be employed in the in vitro embodiment. As above, the activity or inhibition of activity of a collection of similarly acting enzymes (esterase or esterase-like functions) may be utilized in the analysis.

At step 110, biochemical constituents in the saliva sample are characterized. This step generally includes measuring the overall protein content of the sample as related above in the in vivo embodiment, preferably using the technique outlined by Lowry et al or in the alternative any suitable process. Since the saliva samples in the in vitro embodiment are used to characterize hazardous agents from external or outside sources (not directly in the acquired saliva sample), the biomarkers or other biochemical constituents to be analyzed, detected, and monitored in this embodiment are generally characterized to insure that the saliva sample is free from hazardous agents which may interfere with subsequent analysis. For example, the relative specific activity (relative to a selected protein concentration which may or may not be only the catalyzing enzyme concentration) of particular biomarker enzymes may be determined in this step if the particular enzymes are to be analyzed or monitored in subsequent steps.

Step 110 may include an additional purification step (not shown) wherein the saliva sample is purified to remove water or certain chemical or biochemical constituents which may interfere with subsequent steps.

At step 120 a hazardous agent-containing sample, or a sample which potentially contains hazardous agents, is acquired, obtained, or otherwise provided. The hazardous agent-containing specimens or samples may be obtained from milk, urine, feces, blood, plasma, body tissue, water, food, air, soil, another saliva sample, or other source. Step 120 may also comprise extraction, separation, concentration, or purification of the hazardous-agent-containing sample. Such extraction and concentration can take many forms. For example, air samples which potentially contain airborne hazardous agents may be bubbled through water or other aqueous or non-aqueous solution, followed by passing the water through a solid phase absorption column with a hydrophobic phase such as a cyclohexyl solid phase, and eluted through with alcohol or other organic solvent. Hazardous agent-containing samples may similarly be obtained from water, soil, biological fluids, and tissues by extracting with organic or aqueous solvents and absorption column separation, followed by solvent removal. A method for extracting samples from tissue specimens is related by Knaak et al. in "Development of in Vitro $V_{max}$ and $K_m$ Values for the Metabolism of Isophenos by P-450 Liver Enzymes in Animals and Human", *Toxicology and Applied Pharmacology*, Vol. 120, pp. 106–113 (1993), which is herein incorporated by reference.

At step 130, the hazardous (or even non-hazardous if desired) agent-containing sample is combined with or added to the saliva sample, and the combined samples are incubated. The incubation in this step allows hazardous agents to interact with biomarkers. The incubation preferably is carried out at about 37° C. in a water bath, but other appropriate temperatures are contemplated to within the realm of this disclosure. As with the in vivo embodiment, the incubation time may be varied depending upon the particular biomarkers and chemical or biochemical constituents to be analyzed.

At step 140, chemical or biochemical constituents present in the combined samples are analyzed. The analyzing step generally comprises the detection and monitoring of levels or concentrations of one or more biochemical constituents. As in the in vivo embodiment related above, biochemical constituents analyzed in this step may include reactive substrates specific for biomarker enzymes, the biomarker enzymes themselves, reaction products of the substrates, substrates themselves, or any chemicals, proteins, or biomolecules present in the saliva sample. Preferably, spectrophotometric or chemical detection and monitoring means are employed.

The in vitro embodiment, as with in vivo embodiment, preferably involves monitoring the inhibition of biomarker enzymes by hazardous agents by detection and monitoring the reaction product(s) or substrate(s) of the biomarker enzymes with a specific selected substrate or substrate. Again, for reasons of clarity, analyzing step 140 is shown as sub-steps to illustrate the presently preferred in vitro embodiment.

At subs-step 142, one or more reactive substrates specific for or at least acted upon by one or more biomarker enzymes are added to the combined samples from step 130, to serve as biochemical constituents to be analyzed. The added reaction substrate preferably forms easily detectable reaction products upon reaction with its specific biomarker enzyme. One preferred use of the in vitro embodiment involves addition of the substrate p-nitrophenylvalerate, which reacts with the biomarker enzyme carboxylase and forms the hydrolysis product p-nitrophenol which can be detected and monitored spectrophotometrically at 400 nm. Similarly, the substrate acetylthiocholine iodide may be added to the combined samples and hydrolyzed by acetylcholinesterase to yield, upon reaction with added 5,5-dithiobis-2-nitrobenzene, a product detectable at 405 nm.

An incubation sub-step 144 is preferably included in analyzing step 140. The combined samples, together with the added substrates, are incubated at about 37° C. (or other suitable temperature) in a temperature controlled bath for an incubation period which is varied depending upon the reactive substrate and biomarker enzymes being analyzed. Further, ambient temperature incubation or no incubation at all may suffice.

At sub-step 146, the reaction products from the specific substrate and biomarker enzyme are detected and monitored, usually by visible spectrophotometric means as related above. The detection and monitoring indicates the level or concentration of the reaction products, reaction substrates, or other biochemical constituents present in the saliva sample. The activity of the biomarker enzyme in the combined samples from step 130 can be calculated from the level or concentration of reaction product or remaining substrate obtained in this sub-step.

At step 150, the levels or concentrations of the biochemical constituents are compared to standard or baseline levels for the biochemical constituents which are obtained from control or standard samples or specimens. The standard or base line level is preferably in the form of a standard curve. In the preferred in vitro embodiment, the standard curve is one for biomarker enzyme activity which is obtained by inhibition studies in a plurality of control saliva samples. Comparison of the biomarker enzyme activity from the test sample to the standard curves accurately indicates the presence and amount of particular hazardous agents.

The in vitro embodiment may also include the step of determining the base line levels of the biochemical constituents to be used in the comparing step 30. As in the in vivo embodiment, this step is generally carried out by adding test compounds or hazardous agents to control samples and incubating, followed by analyzing biochemical constituents in the sample, preferably in the form of substrate reaction products as related above. A biomarker enzyme activity standard curve is prepared from data from the control samples, and used in the comparing step 150.

Using the in vitro embodiment of the present invention, hazardous agents present from in vitro or otherwise external sources can be detected, quantified, and evaluated by adding the hazardous agent-containing samples to previously characterized saliva samples. Preferably, the biomarkers employed in the in vitro embodiment are acetylcholinesterase and carboxylase (or carboxypeptidase or a combination of these and other enzymes), which are inhibited by IFP, DNIO, and paraoxon organophosphates. The in vitro embodiment allows very sensitive detection of low amounts of these materials in air, water, soil, biological fluid samples, and similar materials. The several other hazardous agents related above which inhibit acetylcholinesterase and carboxylase may also be detected and quantified using the in vitro embodiment.

While the in vitro embodiment is described herein for the inhibition acetylcholinesterase and carboxylase(and usually other similarly acting enzymes present in the saliva), it is contemplated that the in vitro embodiment, like the in vivo embodiment, may also be used to evaluate a variety of hazardous agents through analysis of a variety of biochemical constituents. Thus, the in vitro embodiment of the invention may be employed to detect a variety of hazardous agents, including organophosphates, carbamates, or other pesticides, nerve agents, mustard agents, biotoxicants, heavy metals, endogenous compounds, viruses, mycoplasmas, bacteria, parasites, yeast, and fungus. These agents may be detected in environmental specimens such as air, water, and soil, in food samples, and in biological fluid and tissue samples. The in vitro embodiment can be used to detect and evaluate organ or tissue malfunctions by extracting samples from tissue or biological fluids and combining with a purified and characterized saliva sample as related above, and detecting endogenous compounds resulting from the malfunction. Residual hazardous agents in tissue or biological fluids, and toxic metabolites of the hazardous agents may also be evaluated using this embodiment.

A kit may be provided for home or field use of the in vitro embodiment of the invention. Such a kit would include, in the case of carboxylase (or other like enzyme or combination of enzymes) as a biomarker for example, suitable p-nitrophenylvalerate or equivalent solution, suitable buffer solutions, p-nitrophenol standard solution, and purified carboxylase (or other like enzyme or combination of enzymes) from saliva. A portable constant-temperature bath and visible spectrophotometer may also be included, but the kit may be utilized without a constant-temperature bath.

EXPERIMENTAL

I. Measuring Carboxylase (CE) Activity in Saliva and $EC_{50}$ for Inhibition by Pesticides The protein in 50 μL aliquot of saliva is measured by using bovine serum albumin as a reference standard (Lowery et al., 1951). Briefly, a color was developed by the reaction of protein in saliva and the reagents. The sample was read by a spectrophotometer at 540 nm. The values for the protein standard curve and protein in saliva are shown in Tables 1–2 and FIG. 3. Saliva generally contains about 0.2–0.5% protein, and the exact protein measurement (content) in saliva is needed for calculating the specific activity for the enzymes (specific in the sense of specific to the total measured protein concentration or volume of saliva used).

The carboxylase activity in saliva samples is monitored by the hydrolysis of p-nitrophenylvalerate to the readily detectable p-nitrophenol. The concentration of p-nitrophenol in the sample is measured spectrophotometrically at 400 nm, and the value is calculated from p-nitrophenol standard curve (Table 3 and FIG. 4). Values for carboxylase activity in saliva (nmol. min-1 per mL of saliva) are presented in Tables 4–8 and showing in FIG. 5 and FIG. 6. The average specific activity for carboxylase in human saliva is about 47 nmol $min^{-1}$ per mL.

The assay for carboxylase consists of 4 mL of tris-HCI buffer (pH 7.0) that contain 25 μL of p-nitrophenylvalerate (13.8 mg/mL of alcohol) and 50–500 μL of human saliva. The sample is incubated in water bath for about 20–60 min at about 37° C. In the inhibition study, the agent is incubated with saliva for about 15–20 minutes before the addition of p-nitrophenylvalerate. The values for percents enzyme inhibition by organophosphate are presented in Tables 5–8 and shown in FIG. 7 and FIG. 8. Organophosphate concentration is verified by gas chromatography using standard methods as described by Knaak et al.(1993). DNIO concentration produced 50% inhibition is 2.9 ng per mL (3 PPB).

The use of carboxylase in human saliva to detect the presence of DNIO in water or biological fluid (3 ng/ml) is 3500 times more sensitive than measuring DNIO by GC method.

The kit for carboxylase assay in saliva using this invention will usually consist of p-nitrophenylvalerate or an equivalent as a substrate, tris-HCI buffer (pH 7.0) or an equivalent, purified carboxylase enzyme from human or animal saliva (1 Unit),and p-nitrophenol as standard. The test is performed at about 37° C. in a water bath or at room or other suitable temperature. By way of example, each test may requires 0.35 mg of p-nitrophenylvalerate in 3 mL of phosphate buffer, pH 7.0 and about 0.2–1 mL of saliva. Sample can be incubated at room temperature, about 37° C., other selected temperature in a water bath for about 10–30 minutes. Generally, samples are read using a spectrophotometer at 400 nm. For quality control, 0.05 IU (or other acceptable amount) of purified human or animal saliva enzyme is used as a standard per assay. For monitoring the presence of pesticides in milk, biological fluids, water, and other environmental samples, the cyclohexyl solid phase absorption column (or like procedure) is used to extract and concentrate the chemicals utilizing standard methods as described by Knaak et al.(1993). P-450 liver enzymes and cofactors are used to convert organic phosphothionate to oxon as described by Knaak et al. (1993) to increase sensitivity of the procedure and to decrease the detection limit for this class of chemicals and other chemicals that requires activation by liver enzymes.

TABLE 1

Bovine Serum Albumin (BSA) Absorbance data

| Sample # | BSA μg/tube | (A) at 540 nm | (B) at 640 nm | Average |
|---|---|---|---|---|
| 1 | 25 | 0.158 | 0.168 | 0.168 |
| 2 | 50 | 0.282 | 0.285 | 0.284 |
| 3 | 75 | 0.420 | 0.412 | 0.416 |
| 4 | 100 | 0.520 | 0.530 | 0.525 |
| 5 | 125 | 0.640 | 0.630 | 0.635 |

TABLE 2

Protein Content of Human Saliva*

| Sample # | (A) at 540 nm | (B) at 540nm | (C) at 540nm | Mean | μg protein /sample | mg protein /mL | % |
|---|---|---|---|---|---|---|---|
| IC1 | .343 | .435 | .343 | .374 | 71.2 | 2.848 | .28 |
| IC2 | .62 | .702 | .795 | .706 | 134.5 | 5.379 | .54 |
| IC3 | .502 | .540 | .560 | .534 | 101.7 | 4.069 | .41 |
| IC4 | .415 | .450 | .420 | .428 | 81.5 | 3.261 | .33 |
| IC5 | .202 | .220 | .210 | .211 | 40.2 | 1.608 | .16 |

*Saliva samples were obtained from a 41 years old, adult male. A volume of 25 μL of each sample was used for each assay.

TABLE 3 p-nitrophenol Absorbance Data

| Sample # | μg/tube | nmol/tube | (A) at 400 nm | (B) at 400 nm | Average |
|---|---|---|---|---|---|
| Blank | 0 | | | | |
| 1 | 1.7 | 7.19 | .04 | .036 | .038 |
| 2 | 3.5 | 14.38 | .083 | .088 | .086 |

TABLE 3-continued p-nitrophenol Absorbance Data

| Sample # | μg/tube | nmol/tube | (A) at 400 nm | (B) at 400 nm | Average |
|---|---|---|---|---|---|
| 3 | 7.0 | 28.76 | .160 | .158 | .159 |
| 4 | 14 | 57.51 | .330 | .330 | .330 |
| 5 | 21 | 86.27 | .518 | .518 | .518 |
| 6 | 28 | 115.03 | .750 | .755 | .753 |

*p-nitrophenol 0.125 mL (10 pmol/mL, molecular weight = 139.1) in 25 mL 0.02 N NaOH., Sigma lot # 110H5005, $C_6H_5NO_3$. Final concentration = (0.125 * 10)/25 = 50 nmol/ml, or 6.95 μg/ml.

TABLE 4

Carboxylase Activity In Human Saliva*

| Tube # | (A) at 400 nm | (B) at 400 nm | Net Average | μL saliva** | μg protein** | Activity nmol/min |
|---|---|---|---|---|---|---|
| 1 | .01 | .01 | 0 | 0 | 0 | 0 |
| 2*** | .03 | .02 | 0 | 200 | 570 | 0 |
| 3 | .08 | .09 | .06 | 20 | 57 | .44 |
| 4 | .17 | .14 | .13 | 40 | 114 | .96 |
| 5 | .22 | .28 | .22 | 60 | 171 | 1.70 |
| 6 | .42 | .37 | .38 | 80 | 228 | 2.89 |
| 7 | .63 | .60 | .59 | 100 | 285 | 4.48 |
| 8 | 1.00 | .94 | .94 | 150 | 427 | 6.99**** |
| 9 | 2+ | 2+ | 2+ | 200 | 570 | 15.28 |

*Incubation time 20 minutes and volume of media was 4 mL in phosphate buffer, pH 7.0.
**Protein concentration in saliva = 2.848 mg/ml
***No substrate
****Carboxylase Activity (nmol. $min^{-1}$)per mg protein = 18.8

TABLE 5

Inhibition of Carboxylase in Human Saliva by pesticides (test #1)*

| Sample # | Treatment | Organophos. μg/mL | Absorb. at 400 nm for 20 min. | Absorb. at 400 nm for 60 min. | % Inhib. |
|---|---|---|---|---|---|
| 10 | Paraoxon in Tris/Citrate | 29 | .03 | .14 | 99 |
| 11 | Tris/Citrate | 0 | .58 | 2 | 71 |
| 12 | Alcohol | 0 | 2** | 2 | 0 |
| 13 | Isofenphos | 500 | .33 | .75 | 84 |
| 14 | DSN-Isofenphos-oxon | 175 | .16 | .55 | 92 |

*A 200 μL of saliva (2.484 mg protein/mL) was incubated with the test compound for 15 minutes, then 25 μL of p-nitrophenylvalerate (13.8 mg/mL) was added to the mixture, and the mixture was incubated for 20–60 minutes at 37° C. The organophosphate samples was analyzed by gas chromatography.
**Carboxylase activity (nmol $minute^{-1}$ per mg protein) = 31.0

TABLE 6

Inhibition of Carboxylase in Human Saliva by Pesticides (Test #2)*

| Sample # | Absorb. at 400 nm for 20 min. | Absorb. at 400 nm for 65 min. | Absorb. at 400 nm for 100 min. | Organo-phosphate treatment | μg/ mL | % Act. |
|---|---|---|---|---|---|---|
| 1 | 0 | 0 | 0 | Blank | 0 | 100 |
| 3** | .53 | +2.0 | 2.0 | Alcohol | 0 | |
| 4 | .60 | 2.0 | 2.0 | Isofenphos | 60 | 92 |
| 5 | .47 | 1.1 | 1.5 | Isofenphos | 60 | |

TABLE 6-continued

Inhibition of Carboxylase in Human Saliva by Pesticides (Test #2)*

| Sample # | Absorb. at 400 nm for 20 min. | Absorb. at 400 nm for 65 min. | Absorb. at 400 nm for 100 min. | Organophosphate treatment | µg/mL | % Act. |
|---|---|---|---|---|---|---|
| 6 | .30 | .55 | .64 | DNIO | 5 | 35 |
| 7 | .27 | .57 | .69 | DNIO | 5 | |
| 8 | .23 | .68 | .76 | Paraoxon | 22 | 40 |
| 9 | .23 | .70 | .76 | Paraoxon | 22 | |

*A 50 µL of saliva (4.069 mg/ml) was used in 4 mL phosphate buffer pH 7.0 with a 25 µL of p-nitrophenylvalerate (13.8 mg/mL). Saliva sample was incubated with organophosphate or alcohol for 20 minutes before the addition of substrate.
**Carboxylase activity (nmol minute$^{-1}$ per mg protein) = 17.0

TABLE 7

Inhibition of Carboxylase In Human Saliva by DESN-Isofenphos-Oxon (Test #1)*

| Sample # | DINO ng/mL | Absorb. at 400 nm for 20 min. | Absorb. at 400 nm for 40 min. | Absorb. at 400 nm for 80 min | % Activity | % Inhibition |
|---|---|---|---|---|---|---|
| 1 | Blank | 0 | 0 | 0 | 0 | |
| 2 | Blank | 0 | .01 | 0 | 0 | |
| 3 | 0 | .17 | .33 | .62** | 100 | 0 |
| 4 | 625 | .05 | .07 | .10 | 16 | 84 |
| 5 | 312 | .04 | .06 | .08 | 13 | 87 |
| 6 | 156 | .02 | .02 | .03 | 6 | 95 |
| 7 | 78 | .02 | .02 | .02 | 3 | 97 |
| 8 | 52 | .03 | .03 | .03 | 5 | 95 |
| 9 | 26 | .02 | .03 | .02 | 3 | 97 |
| 10 | 0 | .2 | .20 | .65 | 100 | 0 |

*A 100 µL of saliva (1.608 mg protein/ml) was added to the mixture. The saliva was incubated with DNIO for 15 minutes at 37° C. before adding 25 µL p-nitrophenylvalerate (13.8 mg/ml of alcohol). Total volume of media was 4 mL in phosphate buffer pH 7.0
**Carboxylase activity (nmol minute$^{-1}$ per mg protein) = 7.4

TABLE 8

Inhibition of Carboxylase In Human Saliva by DSN-Isofenphos-Oxon (Test #2)*

| Sample # | DINO ng/mL | Absorb. at 400 nm | nmol/min per mg protein | % Activity | % Inhibition |
|---|---|---|---|---|---|
| 1 | Blank | 0 | 0 | 0 | |
| 2 | Blank | 0 | 0 | 0 | |
| 3 | 0 | .8 | 13.09 | 100 | 0 |
| 4 | 0 | .8 | 13.09 | 100 | 0 |
| 5 | 8.6 | .32 | 5.24 | 40 | 60 |
| 6 | 2.9 | .40 | 6.55 | 50 | 50 |
| 7 | 1.0 | .46 | 7.46 | 57 | 43 |
| 8 | .3 | .62 | 10.21 | 78 | 22 |
| 9 | .1 | .66 | 10.87 | 83 | 17 |
| 10 | .04 | .75 | 12.31 | 94 | 6 |

*A 0.2 mL of saliva (1.608 mg/ml) was incubated for 15 minutes with DNIO at 37° C., then 25 µL of p-nitrophenylvalerate (13.8) was added to the mixture and incubated for 30 minutes. Volume of media = 4 mL phosphate buffer pH 7.0

II. Procedure for measuring Acetylcholinesterase (AChE) Activity in Saliva and EC$_{50}$ for inhibition by Pesticides The hydrolysis of acetylthiocholine iodide (an analog of acetylcholine iodide) by the saliva enzyme or enzymes is measured by generating the yellow 5-thio-2-nitrobenzoate with an absorbance maximum at 405 nm. The rate of change of absorbance is directly proportional to acetylcholinesterase activity. In this procedure, 0.1–1 mL of saliva (3.261 mg protein/mL) is incubated with 100 µL of acetylthiocholine iodide (0.018M) (lot #10H0653 Sigma) for 30–180 minute at 37° C. in 4.0 mL phosphate buffer (pH 7.8). After the incubation, a 0.2 mL of DTNB is added and the sample is read at 405 nm. The enzyme activity is calculated from glutathione standard curve (Table 9 and FIG. 9). Values for AChE activity in human saliva and enzyme kinetics are presented in Tables 10–14 and show in FIG. 10 through FIG. 14.

The AChE specific activity in saliva is about 4 nmol minute$^{-1}$ per mL of saliva. In the inhibition study for AChE by organophosphate, saliva is incubated with the inhibitor for about 15 minutes before adding the substrate. The percent of enzyme inhibition by organophosphate is calculated and presented in Tables 13–14 and showing in FIG. 15. A 3 ng DNIO per mL produced 50% inhibition in AChE which is 3500 times more sensitive than the delectability limit for DNIO by gas chromatography (10,000 ng/mL).

Monitoring the presence of pesticides in milk, biological fluids, water, and other environmental samples may require the use of cyclohexyl solid phase absorption column to extract and concentrate the chemicals such as described by Knaak et al.(1993). P-450 liver enzymes and cofactors is used to convert organic phosphothionate to oxon such as described by Knaak et al.(1993) to increase sensitivity of the procedure and to decrease the detection limit for this class of chemicals and other chemicals that requires activation by liver enzymes. The exposure to other agents that inhibit cholinesterase are also evaluated by this procedure. These agents include: (a) Other organophosphate insecticides, (b) carbamate insecticides, (c) blue green algae-anatoxicant-A (s), (d) solanum specious black nightshade (S. nigrum), potato (S. tuberosum), horse nettle (S. tubemsum), European bittersweet (S. dulcamara), Jerusalem cherry (S. pseudocapsicum)}, (e) other noninfectious agents, and 6) infectious agents.

TABLE 9

Glutathione (GSH) Standard Curve*

| Sample # | Absorb. at 405 nm (A) | Absorb. at 405nm (B) | Average | GSH µg | GSH nmol |
|---|---|---|---|---|---|
| 1 | .072 | .070 | .071 | 3.84 | 12.5 |
| 2 | .182 | .187 | .185 | 7.68 | 25.0 |
| 3 | .188 | .240 | .214 | 11.52 | 37.5 |

TABLE 9-continued

Glutathione (GSH) Standard Curve*

| Sample # | Absorb. at 405 nm (A) | Absorb. at 405nm (B) | Average | GSH µg | GSH nmol |
|---|---|---|---|---|---|
| 4 | .258 | .33 | .294 | 15.37 | 50.1 |
| 5 | .360 | .39 | .375 | 23.05 | 75.1 |
| 6 | .435 | .460 | .447 | 30.73 | 100 |
| 7 | .820 | .820 | .820 | 61.46 | 200 |

*Glutathione = 0.0154 g/50 mL EDTA working buffer or 15.4 mg/50 mL.

TABLE 10

Carboxylase Activity in Human Saliva sample used for Cholinesterase measurement

| Sample # | Saliva µL* | Phosphate Buffer mL | p-nitro-phenyl-valerate µL | Absorb. at 400 nm for 5 min. | Absorb. at 400 nm for 15 min. | Absorb. at 400 nm for 22 min. | Absorb. at 400 nm for 40 min.** |
|---|---|---|---|---|---|---|---|
| 1 | 50 | 3.95 | 0 | 0 | 0 | 0 | 0 |
| 2 | 50 | 3.95 | 25 | 1 | .35 | .48 | 1.0 |

*Protein concentration = 3.261 mg/ml, 0.163 mg per sample.
**Carboxylase Activity (nmol minute$^{-1}$ per mg protein) = 24.1 and Carboxylase Activity (nmol minute$^{-1}$ per mL of saliva) = 78.6 or 0.8 IU per 100 mL.

TABLE 11

Acetylcholinesterase Activity In Human Saliva (test #1).

| Tube # | Sub. µL | DTNB µL | Buffer mL | Saliva mL* | Absorb. at 405 nm for 55 min. |
|---|---|---|---|---|---|
| 1 | 100 | 100 | 3.8 | 0 | 0 |
| 2 | 100 | 100 | 3.8 | 0 | 0 |
| 3 | 100 | 100 | 2.8 | 1 | More than 2** |
| 4 | 100 | 100 | 2.8 | 1 | 1.5 |

*Protein concentration in saliva = 3.261 mg/ml, sample was incubated at 37° C.
**Acetyl Cholinesterase Activity (nmol. min$^{-1}$ per mg protein) = 2.183

TABLE 12

Acetylcholinesterase Activity in Human Saliva (Test #2)

| Sample # | Saliva µL | Treat. Type | Absorb. at 405 nm for 50 min. | Absorb. at 405 nm for 110 min. | Absorb. at 405 nm for 165 min. | Activity in nmol/min |
|---|---|---|---|---|---|---|
| 1 | Blank | 0 | .01 | .01 | 0 | 0 |
| 2 | 25 | 0 | .03 | .02 | .03 | .06 |
| 3 | 50 | 0 | .08 | .08 | .10 | .20 |
| 4 | 75 | 0 | .10 | .12 | .17 | .34 |
| 5 | 100 | 0 | .16 | .21 | .29 | .58 |
| 6 | 125 | 0 | .18 | .26 | .36 | .72 |
| 7 | 150 | 0 | .22 | .30 | .43 | .86 |
| 8 | 175 | 0 | .24 | .37 | .50 | 1.00 |
| 9 | 200** | 0 | .27 | .42 | .57 | 1.14 |
| 10 | 200 | IFP*** | .41 | .43 | .51 | 1.02 |
| 11 | 200 | DNIO | .14 | .10 | .11 | .22 |

*Substrate: Acetylthiocholine iodide, 0.018M (lot #10H0653, Sigma), 0.2603 g in 50 mL distilled water = 5.206 mg/ml; 100 µL was used. Protein concentration in saliva = 3.261 mg/ml. Incubation media is 4.0 mL of phosphate buffer(pH 7.0), and incubation temperature was 37° C.
**Cholinesterase activity (nmol. min$^{-1}$ per mg protein) = 1.09
***Inhibitor volume = 25 µL contain 240 µg of isofenphos or 2 µg of DNIO.

TABLE 13

Inhibition of Acetylcholinesterase In Human Saliva by DESN-ISOFENPHOS OXON (Test #1)

| Tube #* | Saliva mL | Inhibitor mL | Absorb. at 405 nm (n = 2) for 35 min. | Absorb. at 405 nm for 55 min. | Absorb. at 405 nm for 100 min. |
|---|---|---|---|---|---|
| 1 | 0 | DTNB | 0 | 0 | 0 |
| 2 | 1 | DTNB | .06 | 0 | 0 |
| 3 | .2 | 0 | .11 | .14 | .21 |
| 4 | .3 | 0 | .22 | .24 | .38 |

TABLE 13-continued

Inhibition of Acetylcholinesterase In Human Saliva by DESN-ISOFENPHOS OXON (Test #1)

| Tube #* | Saliva mL | Inhibitor mL | Absorb. at 405 nm (n = 2) for 35 min. | Absorb. at 405 nm for 55 min. | Absorb. at 405 nm for 100 min. |
|---|---|---|---|---|---|
| 5 | .4 | 0 | .18 | .24 | .44 |
| 6 | .5 | 0 | .23 | .33 | .55 |
| 7 | .6 | 0 | .26 | .42 | .73 |
| 8 | .8 | 0 | .36 | .55 | 1.30 |
| 9 | 1.0 | 0 | .46 | .75 | 2.00 |
| 10 | 1.0 | 0 | .55 | .85 | 2.00 |

TABLE 13-continued

Inhibition of Acetylcholinesterase In Human Saliva by DESN-ISOFENPHOS OXON (Test #1)

| Tube #* | Saliva mL | Inhibitor mL | Absorb. at 405 nm (n = 2) for 35 min. | Absorb. at 405 nm for 55 min. | Absorb. at 405 nm for 100 min. |
|---|---|---|---|---|---|
| 11 | 1.0 | DNIO** | .04 | .08 | .03 |
| 12 | 1.0 | DNIO | .07 | .04 | .03 |

*100 µL of Acetylthiocholine solution was added to phosphate buffer (pH 7.8), total volume = 4 mL.
**A 25 µL of DNIO (4 µg) solution was added to mixture.

TABLE 14

Inhibition Acetylcholinesterase In Human Saliva by DESN-Isofenphos-Oxon. (Test #2)*

| Sample # | DNIO ng/mL | Absorb. at 408 nm for 65 min. | Absorb. at 408 nm for 180 min. | nmol/min per mg | % Activity | % Inhibition |
|---|---|---|---|---|---|---|
| 1 | 0 | .01 | .01 | | | |
| 2 | 0 | .19 | .32 | .41 | 100 | 0 |
| 3 | 0 | .19 | .31 | .41 | 100 | 0 |
| 4 | 625 | .07 | .03 | .04 | 10 | 90 |
| 5 | 313 | .07 | .03 | .04 | 10 | 90 |
| 6 | 156 | .10 | .04 | .05 | 13 | 87 |
| 7 | 78 | .10 | .04 | .05 | 13 | 87 |
| 8 | 52 | .09 | .04 | .05 | 13 | 87 |
| 9 | 26 | .11 | .06 | .08 | 19 | 81 |
| 10 | 8.6 | .11 | .08 | .11 | 26 | 74 |
| 11 | 2.9 | .16 | .14 | .19 | 45 | 55 |
| 12 | 1.0 | .17 | .21 | .29 | 68 | 32 |
| 13 | .3 | .21 | .26 | .34 | 84 | 16 |
| 14 | .1 | .14 | .28 | .37 | 90 | 10 |
| 15 | .04 | .17 | .29 | .39 | 94 | 6 |

*DESN-Isofenphos-Oxon (DNIO) was incubated for 30 minutes with saliva before the addition of acetylthiocholine substrate at room temperature. Total volume = 4 mL phosphate buffer (pH 7.8), saliva volume = 0.6 mL, protein concentration = 1.608 mg/ml, protein per incubation = 1.008 mg.

III. Monitoring Milk, Biological fluids, Water, and Environmental samples for toxicants using saliva biomarkers.

The presence of chemicals in milk, water, urine and other biological fluids are detected using saliva enzymes. The detection limit for the chemicals depends on the chemical potency and the number of chemicals present in the sample. The data presented here using saliva enzymes indicates a remarkably low concentration of des N-isofenphos (DNIO) in water (3 ng/mL) is detectable using the saliva enzyme method. A 50% inhibition of esterase activity is produced at 3 ng/mL DNIO. In this procedure, the sample is passed through cyclohexyl solid phase absorption column (C-18) to extract and concentrate the chemicals as described by Knaak et al.(1993). The retention of the chemicals on C-18 column depends on their lipid solubility. The non-polar compounds usually have the highest retention. Then, the chemical is eluted with 1 mL of alcohol. A 0.1 mL of the elute is tested for the inhibition of saliva enzymes as described in this application. Toxicants in solid environmental samples, fruit and vegetables can be extracted with water or proper solvent. Samples of the extract are tested for enzymes inhibition. The inhibition of saliva enzyme indicates the presence of toxicant(s) in the sample and further analysis is needed to identify the specific chemical(s).

IV. Using Saliva biomarkers to evaluate toxicity of chemical and biological agents in vitro.

Purified saliva enzymes from human and animals can be used as inexpensive and sensitive tools to screen for toxicity of agents that inhibit one or more enzyme system in saliva. This procedure can be used in research and in chemical production setting replacing the need of using experimental animals. The use of animals in toxicity testing is expensive and time consuming when compared with the use of the saliva enzymes. In addition, the data collected from animal studies may not accurately predict human toxicity. Using the saliva methods, up to 60 samples can be assayed for enzymes inhibition within one hour.

V. Monitoring the presence of toxic or reactive agents in air.

Toxic or reactive agents in air can be detected by the degree of the inhibition of enzymes or alteration of other biochemicals in saliva in both in vivo biomedical applications and in vitro environmental applications. In the in vivo applications enzymes or other biochemical biomarker activities in saliva are collected from a subject before entering the work area and during and after leaving the work area. In the in vitro environmental applications air samples are collected in a bubbler system containing the suitable trapping solvent, on suitable filters, or by other suitable means. The presence of chemicals that inhibit saliva enzymes or react with other saliva biochemicals are assayed using standard instrumental or chemical techniques. For example, enzyme activity in the presence of pure trapping solvent can assayed and used as a reference standard.

VI. Monitoring the Functioning of Organs

Additionally, the subject invention has use as a method for evaluating organ function by monitoring changes in the chemical composition of saliva. By following the presence and concentration (increases or decreases) of various components in saliva such as enzymes, antibodies, hormones, and the like, the functional state of organs contributing these factors can be monitored.

Accordingly, it will be seen that the present invention provides a method for evaluation of hazardous agents in both in vivo and in vitro applications. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:

1. A method for evaluating the presence of a chemical agent, said chemical agent selected from the group consisting of organophosphate insecticides and carbamate insecticides, comprising the steps of:

a. providing a saliva sample;

b. measuring the total protein content of the saliva sample;

c. adding a reactive substrate specific for a biomarker enzyme, said biomarker enzyme selected from the group consisting of acetylcholinesterase, cholinesterase, alkaline phosphatase, acid phosphatase, amylase, and carboxypeptidase;

d. incubating said saliva sample and said reactive substrate;

e. detecting and measuring the level of a reaction product formed by the reaction between said biomarker enzyme and said substrate; and f. comparing detected level of the reaction product in said saliva sample with those of control samples, calculating activity of said biomarker enzyme from the level of reaction product formation, and determining inhibition of activity of said biomarker enzyme present in said saliva sample, wherein inhibition of activity of said biomarker enzyme is indicative of the presence of said chemical agent in said sample.

2. A method for evaluating the presence of a chemical agent, said chemical agent selected from the group consisting of organophosphate insecticides and carbamate insecticides, comprising the steps of:

a. providing a saliva sample, containing a biomarker enzyme, said biomarker enzyme selected from the group consisting of acetylcholinesterase, cholinesterase, alkaline phosphatase, acid phosphatase, amylase, and carboxypeptidase;

b. measuring the total protein content of the saliva sample;

c. providing a sample containing said chemical agent;

d. combining the sample containing said chemical agent with said saliva sample;

e. adding a reactive substrate specific for said biomarker enzyme;

f. incubating said combined sample and said reactive substrate;

g. detecting and measuring the level of a reaction product formed by the reaction between the biomarker enzyme and the substrate; and h. comparing detected level of the reaction product in said combined sample with those of control samples, calculating activity of said biomarker enzyme from the level of reaction product formation, and determining inhibition of activity of said biomarker enzyme present in said combined sample wherein inhibition of activity of said biomarker enzyme is indicative of the presence of said chemical agent in said sample.

3. A method for evaluating the presence of a chemical agent according to claim 2, wherein the method further comprises the step of extracting and concentrating the sample containing said chemical agent before combining with said saliva sample.

4. A method for monitoring and evaluating a chemical agent according to claim 3, the method further comprising the step of purifying said saliva sample before combining with the sample containing said chemical agent.

5. A method for evaluating the presence of a chemical agent according to claim 4, wherein the method further comprises selecting said chemical agent from specimens selected from the group consisting of milk, urine, feces, blood, plasma, body tissue, water, air, and soil.

* * * * *